(12) United States Patent
Guo et al.

(10) Patent No.: US 9,726,623 B2
(45) Date of Patent: Aug. 8, 2017

(54) GAMMA ANALYSIS OF CEMENT

(71) Applicant: Halliburton Energy Services, Inc, Houston, TX (US)

(72) Inventors: Weijun Guo, Houston, TX (US); Da Luo, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/126,484

(22) PCT Filed: Mar. 17, 2015

(86) PCT No.: PCT/US2015/020946
§ 371 (c)(1),
(2) Date: Sep. 15, 2016

(87) PCT Pub. No.: WO2016/148696
PCT Pub. Date: Sep. 22, 2016

(65) Prior Publication Data
US 2017/0089846 A1    Mar. 30, 2017

(51) Int. Cl.
*G01V 5/12*      (2006.01)
*G01N 23/203*    (2006.01)
*G01N 33/38*     (2006.01)
*E21B 47/00*     (2012.01)

(52) U.S. Cl.
CPC ....... *G01N 23/203* (2013.01); *E21B 47/0005* (2013.01); *G01N 33/383* (2013.01); *G01V 5/12* (2013.01)

(58) Field of Classification Search
CPC ..................................................... G01V 5/125
See application file for complete search history.

(56) References Cited

U.S. PATENT DOCUMENTS

| 2,451,472 | A | 10/1948 | Coggeshall |
| 3,265,151 | A | 8/1966 | Anderson |
| 3,787,686 | A | 1/1974 | Culver |
| 4,947,040 | A | 8/1990 | Mahdavi et al. |

(Continued)

FOREIGN PATENT DOCUMENTS

| EP | 1795919 A2 | 6/2007 |
| WO | WO 2009/088501 A1 | 7/2009 |
| WO | WO 2013/040529 A1 | 3/2013 |

OTHER PUBLICATIONS

Naqvi et al., "Prompt gamma ray evaluation for chlorine analysis in blended cement concrete," 2014, Applied Radiation and Isotopes, vol. 94, pp. 8-13.*

(Continued)

*Primary Examiner* — Kiho Kim
(74) *Attorney, Agent, or Firm* — Haynes and Boone, LLP

(57) ABSTRACT

A method and logging tool for evaluating the cement behind casing. In an embodiment, a collimated source emits gamma rays at selectable elevation angles. A fixed collimated detector received reflected gamma rays. Reflected calibration gamma rays are measured in a wellbore section having a cement layer of known condition. Backscattered evaluation gamma rays are measured in a section of wellbore to be analyzed and are compared with the backscattered calibration gamma rays to provide an indication of the quality of the cement layer at that location.

25 Claims, 9 Drawing Sheets

(56) References Cited

U.S. PATENT DOCUMENTS

| | | | |
|---|---|---|---|
| 5,900,627 A | 5/1999 | Odom et al. | |
| 6,207,953 B1 | 3/2001 | Wilson | |
| 6,766,855 B2 | 7/2004 | Snoga | |
| 6,806,474 B2 | 10/2004 | McGregor et al. | |
| 6,936,812 B2 | 8/2005 | Odom et al. | |
| 7,253,401 B2 | 8/2007 | Mickael et al. | |
| 7,253,402 B2 | 8/2007 | Gilchrist et al. | |
| 7,294,829 B2 | 11/2007 | Gilchrist | |
| 7,361,886 B2 | 4/2008 | Stoller et al. | |
| 8,063,356 B1 | 11/2011 | Zhou et al. | |
| 8,440,961 B2 | 5/2013 | Inanc et al. | |
| 8,455,812 B2 | 6/2013 | Nikitin et al. | |
| 8,476,584 B2 | 7/2013 | Li et al. | |
| 8,598,510 B2 | 12/2013 | Zhang et al. | |
| 8,604,417 B2 | 12/2013 | Gilchrist et al. | |
| 8,700,333 B2 | 4/2014 | Roberts | |
| 2007/0263767 A1* | 11/2007 | Brondo | G01V 5/0069 378/57 |
| 2008/0061225 A1* | 3/2008 | Orban | G01V 5/125 250/269.3 |
| 2008/0116365 A1 | 5/2008 | Flecker | |
| 2010/0223010 A1 | 9/2010 | Nikitin et al. | |
| 2010/0252725 A1* | 10/2010 | Stewart | G01V 5/125 250/269.3 |
| 2011/0198488 A1 | 8/2011 | Stoller et al. | |
| 2012/0075953 A1 | 3/2012 | Chace et al. | |
| 2013/0134304 A1* | 5/2013 | Beekman | G01T 1/40 250/269.6 |
| 2013/0158876 A1 | 6/2013 | Grau | |
| 2013/0206985 A1 | 8/2013 | Turner et al. | |
| 2014/0001350 A1 | 1/2014 | Beekman et al. | |
| 2014/0021359 A1 | 1/2014 | Nakamura et al. | |
| 2014/0042311 A1 | 2/2014 | Zhou et al. | |
| 2014/0124659 A1 | 5/2014 | Berheide et al. | |
| 2014/0374582 A1 | 12/2014 | Guo et al. | |
| 2016/0282505 A1* | 9/2016 | Lee | G01V 5/125 |
| 2016/0291198 A1* | 10/2016 | Lee | G01V 5/125 |

OTHER PUBLICATIONS

Chen, et al., "Compact Electronic Gamma Source for Radiotherapy," Application of Accelerators in Research and Industry, American Institute of Physics Conference Proceedings, 1336, pp. 413-147 (2011).

International Search Report and the Written Opinion of the International Search Authority, or the Declaration, Nov. 3, 2016, PCT/US2015/020946, 16 pages, ISA/KR.

* cited by examiner

GAMMA ANALYSIS OF CEMENT

PRIORITY

The present application is a U.S. National Stage patent application of International Patent Application No. PCT/US2015/020946, filed on Mar. 17, 2015, the benefit of which is claimed and the disclosure of which is incorporated herein by reference in its entirety.

TECHNICAL FIELD

The present disclosure relates generally to oilfield equipment, and in particular to downhole tools, drilling systems, and drilling techniques for drilling wellbores in the earth. More particularly still, the present disclosure relates to logging systems and methods for evaluating one or more characteristics of cement in a wellbore between a casing and the formation.

BACKGROUND

The use of the sonic and ultrasonic waveforms are typically used to evaluate the quality of the cement sheath between wellbore casing and a formation. A logging tool, which may have one or more sonic and/or ultrasonic receivers and one or more sonic and/or ultrasonic transmitters, is lowered into a wellbore and measurements are taken at various depths. Sonic and/or ultrasonic waves are transmitted from the logging tool towards the formation, and reflected from the casing, cement sheath, and formation. The reflected waves are received, recorded, processed, and interpreted to determine the presence, or lack thereof, of cement between the casing and the formation or other wellbore wall.

Recorded sonic waveforms, commonly referred to as a cement bond log, variable display log or micro seismogram log data, may be plotted with respect to wellbore depth and then visually interpreted by an operator to provide a basic understanding of the composition of the cement sheath in the annular space. Cement bond log data may be plotted with waveform arrival time indicated horizontally, wellbore depth indicated vertically, and waveform amplitude indicated by color or intensity, resulting in a serrated or striped display. Adjacent to this cement bond log plot, a waveform amplitude plot and a gamma ray plot may be provided for correlation.

Waveforms generally have a very different signature when passing through an annular space filled with fluid (free pipe) versus solid (cement). The free pipe signature typically includes higher amplitudes, a low rate of attenuation and a consistent waveform. When the annular space is filled with a solid material such as cement, the amplitude of the waveform is reduced, the attenuation of the same waveform is increased, and the waveforms are not consistent.

In other words, there is typically a significant visible difference in the plotted sonic waveform data between a free pipe response and bonded pipe response. Free pipe is indicated by high waveform amplitude, strong casing arrival, straight or consistent waveforms with depth (indicated by regular striping with depth as plotted), and visible chevron patterns at casing joints. A good cement sheath is indicated by attenuated waveform amplitude, weak casing arrival, and inconsistent waveforms with depth (indicated by irregular striping with depth as plotted).

However, interpretation of a partial cement bond, such as the presence of either a channel, mixed cement and drilling fluids, spacers, or a combination thereof, can be more difficult. There is an apparent transition zone between good and poor cement bonds, and identification of and analysis of the bond in such cases relies on the experience and eyes of the analyst to assess if the cement sheath is adequate for continued wellbore completion operations or if remedial work is required.

In addition to the analysis of sonic waveforms, ultrasonic waveform may be used to evaluate the cement sheath by determining either the impedance or attenuation of the material next to the casing itself. The impedance and attenuation of the material is normally mathematically calculated using properties of the casing, cement, mud and other materials in a complicated method requiring extensive knowledge of a routineer in the field.

BRIEF DESCRIPTION OF THE DRAWINGS

Embodiments are described in detail hereinafter with reference to the accompanying figures, in which.

DETAILED DESCRIPTION

Figure 1:
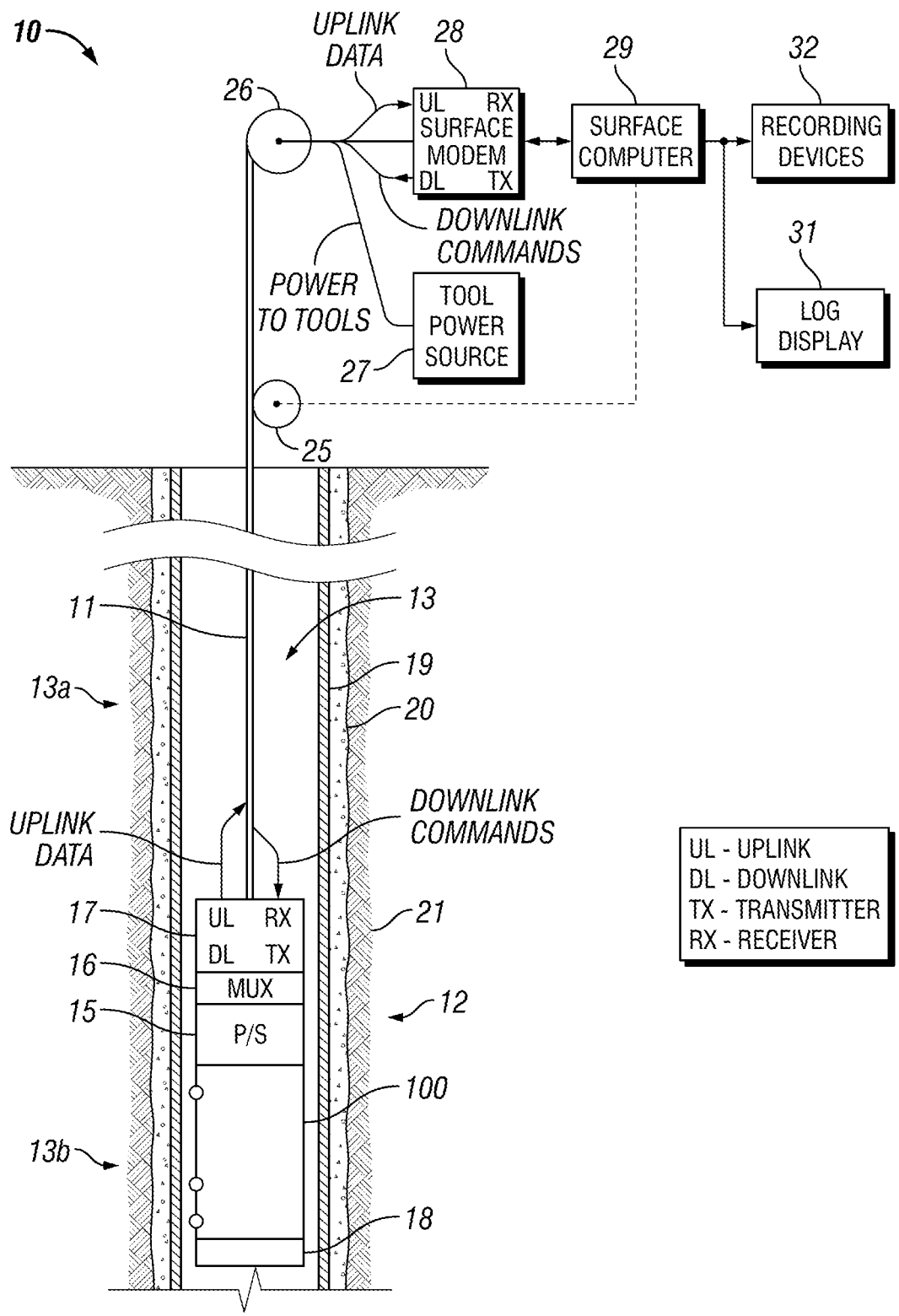
FIG. 1 is a block-level schematic diagram of a well logging system according to an embodiment, showing a logging tool suspended by wireline in a well and incorporating a logging tool, such as that of FIG. 3A.

The present disclosure may repeat reference numerals and/or letters in the various examples. This repetition is for the purpose of simplicity and clarity and does not in itself dictate a relationship between the various embodiments and/or configurations discussed. Further, spatially relative terms, such as "beneath," "below," "lower," "above," "upper," "uphole," "downhole," "upstream," "downstream," and the like, may be used herein for ease of description to describe one element or feature's relationship to another element(s) or feature(s) as illustrated in the figures. The spatially relative terms are intended to encompass different orientations of the apparatus in use or operation in addition to the orientation depicted in the figures.

FIG. 1 shows a system view of a well logging system of the present disclosure. The system shown in FIG. 1 is identified by the numeral 10, which generally refers to a well logging system.

Figure 2:
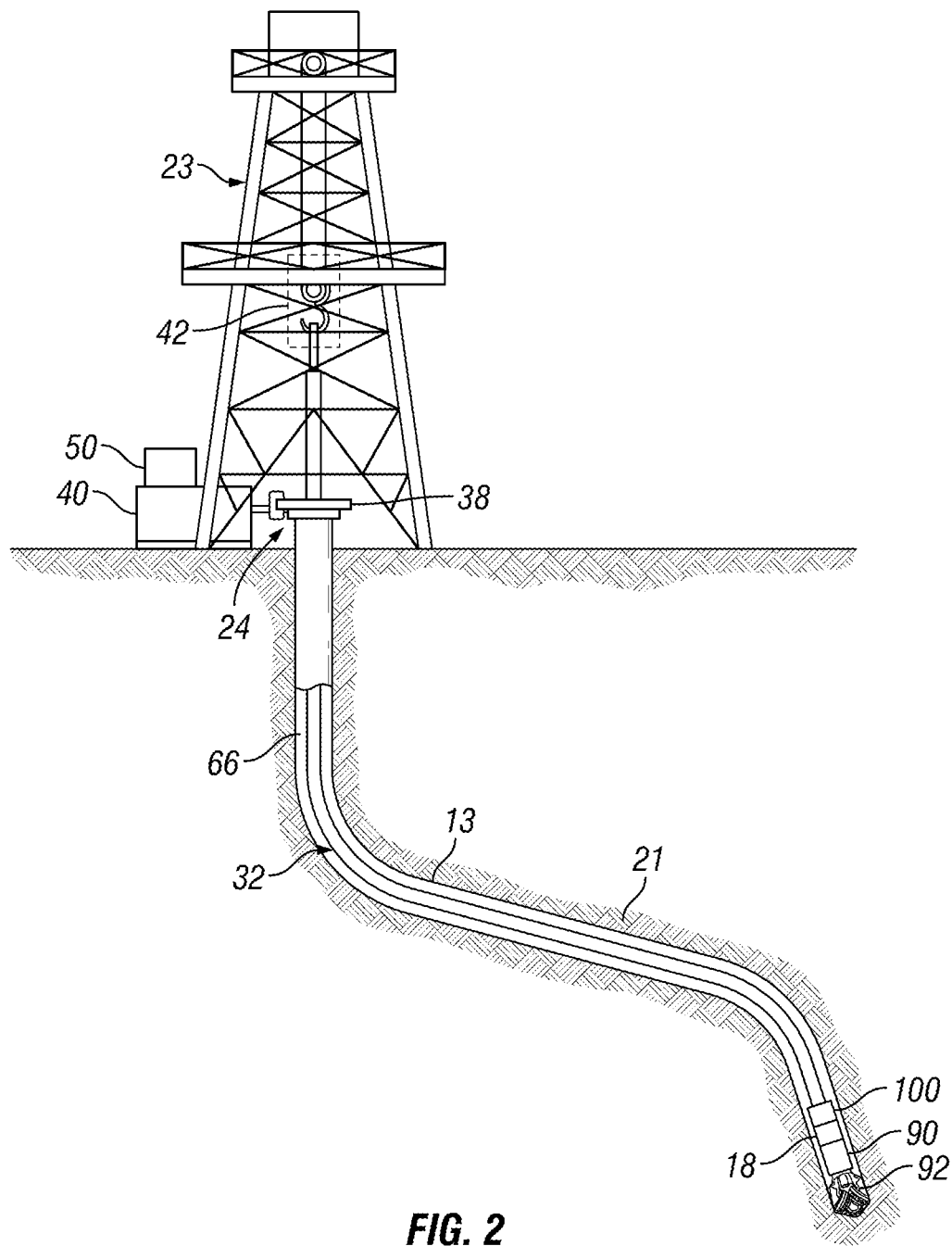
FIG. 2 is a block-level schematic diagram of a logging while drilling system according to an embodiment, showing a drill string and a drill bit for drilling a bore in the earth and a logging tool disposed in a drill string incorporating a logging tool, such as that of FIG. 3A.

A logging cable 11 may suspend a sonde 12 in a wellbore 13. Wellbore 13 may be drilled by a drill bit on a drill string as illustrated in FIG. 2, and wellbore 13 may be lined with casing 19 and a cement sheath 20. For illustrative purposes, a shallow portion 13a of wellbore 13 lacks a proper cement bond, while a deeper portion 13b of wellbore 13 has a good cement bond.

Sonde 12 may have a protective housing which may be fluid tight, be pressure resistant, and support and protect internal components during deployment. Sonde 12 may enclose one or more logging systems to generate data useful in analysis of wellbore 13 or in determining the nature of the formation 21 in which wellbore 13 is located.

In one embodiment, logging tool 100 may be provided, as described below with respect to FIG. 3A, for testing the quality of the bond or other characteristics of cement 20 between casing 19 and formation 21, for example. Other types of tools 18 may also be included in sonde 12. Sonde 12 may also enclose a power supply 15. Output data streams from logging tool 100 and other tools 18 may be provided to a multiplexer 16 located in sonde 12. Sonde 12 may also include a communication module 17 having an uplink communication device, a downlink communication device, a data transmitter, and a data receiver.

Logging system 10 may include a sheave 25, which may be used in guiding logging cable 11 into wellbore 13. Cable 11 may be spooled on a cable reel 26 or drum for storage. Cable 11 may connect with sonde 12 and be let out or taken in to raise and lower sonde 12 within wellbore 13. Conductors in cable 11 may connect with surface-located equipment, which may include a DC power source 27 to provide power to tool power supply 15, a surface communication module 28 having an uplink communication device, a downlink communication device, a data transmitter and receiver, a surface computer 29, a logging display 31, and one or more recording devices 32. Sheave 25 may be connected by a suitable detector arrangement to an input to surface computer 29 to provide sonde depth measuring information. Surface computer 29 may provide an output for logging display 31 and recording device 32. Surface logging system 10 may collect data as a function of depth. Recording device 32 may be incorporated to make a record of the collected data as a function of wellbore depth.

FIG. 2 illustrates a system view of a measurement while drilling (MWD) or logging while drilling (LWD) system of the present disclosure. The system shown in FIG. 2 is identified by the numeral 22, which generally refers to a drilling system.

LWD system 22 may include a land drilling rig 23. However, teachings of the present disclosure may be satisfactorily used in association with offshore platforms, semi-submersible, drill ships, or any other drilling system satisfactory for forming wellbore 13 extending through one or more downhole formations 21.

Drilling rig 23 and associated control system 50 may be located proximate a well head 24. Drilling rig 23 may also include a rotary table 38, rotary drive motor 40, and other equipment associated with operation of drill string 32. Annulus 66 may be defined between the exterior of drill string 32 and the inside diameter of wellbore 13.

Bottom hole assembly 90 or drill string 32 may also include various tools that provide logging or measurement data and other information about wellbore 13. This data and information may be monitored by a control system 50. In particular, logging tool 100 may be provided, as described below with respect to FIG. 3A. Additionally, other various types of MWD or LWD tools 18 may be included.

Figure 3A:
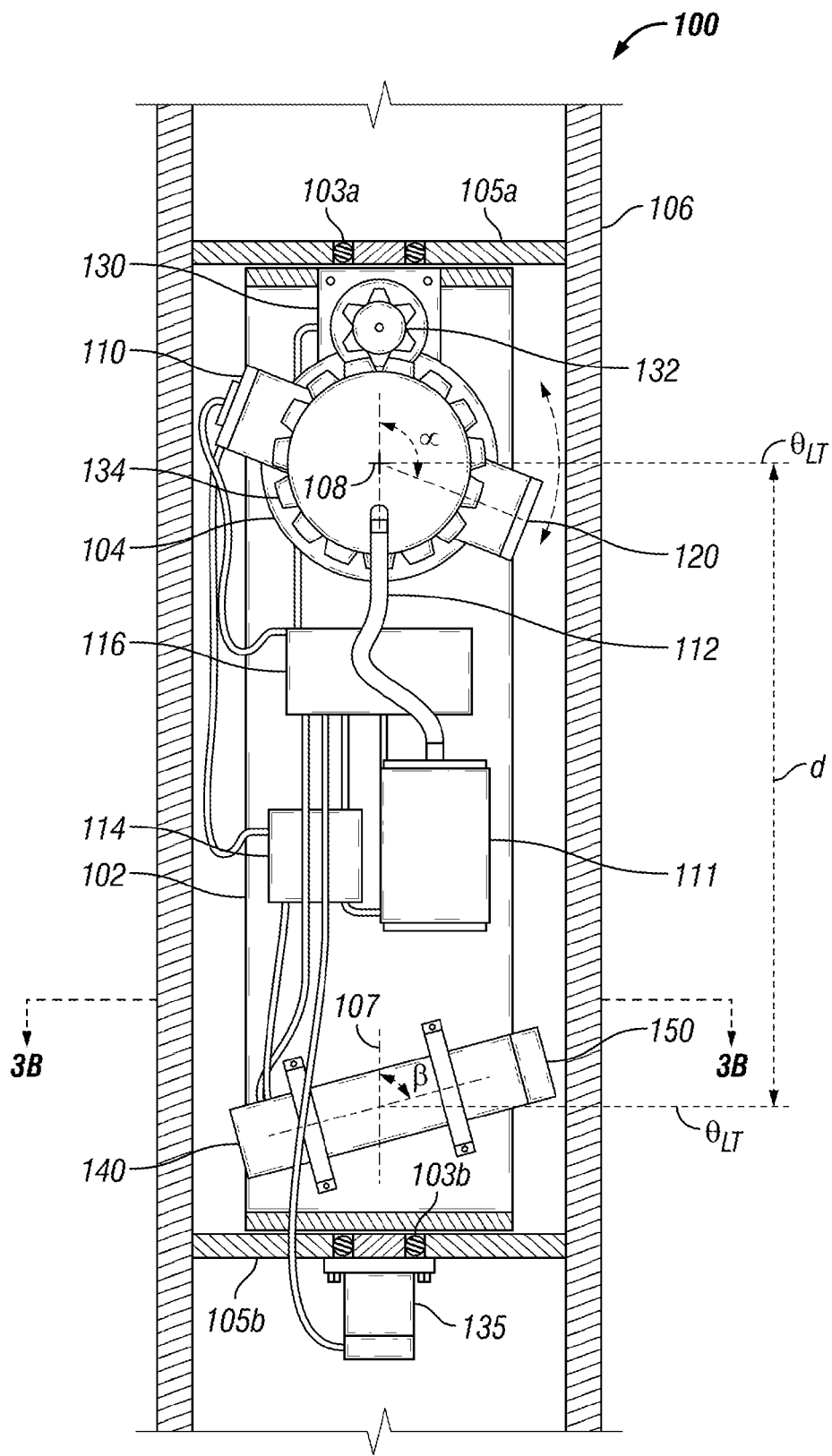
FIG. 3A is an elevation view in axial cross section of a downhole logging tool for evaluating cement according to an embodiment, showing a rotatable collimated gamma ray source and a fixed collimated gamma ray detector.

FIG. 3A is an elevation view in axial cross section of a downhole tool 100 for evaluating bonding and/or other cement characteristics according to an embodiment. Logging tool 100 may include a housing 106, which may be generally cylindrical in shape and dimensioned to fit within wellbore 13. Housing 106 may be defined by sonde 12 (FIG. 1) or a sub for inclusion along drill string 32 (FIG. 2) or the like.

Downhole logging tool 100 may include a gamma ray source 110. In one or more embodiments, gamma ray source 110 may be a compact electronic gamma source, such as that described hereinafter with reference to FIG. 4. However, in other embodiments, another type of gamma ray source 110, such as a selectively shielded radioisotope, may be used. In one or more embodiments, a source collimator 120 may be included as part of gamma ray source 110 to produce collimated source gamma rays. The disclosure is not limited to a particular type of gamma ray source.

According to one or more embodiments, logging tool 100 is disposed to orient collimated source gamma rays at a selectable elevation angle α with respect to housing 106. For instance, gamma ray source 110 may be rotatively mounted to a carriage 102 within housing 106, with a bushing or bearing or 104 for example, to be rotatable about a transverse diameter or chord 108 defined with respect to carriage 102. An elevation actuator 130 may be used to rotate gamma ray source 110 within a range of elevation angles α. Elevation actuator 130 may be directly coupled or indirectly coupled via a mechanical transmission, for example, to gamma ray source 110. Elevation actuator 130 may include a servo motor, a stepper motor, or other suitable device. In the arrangement illustrated in FIG. 3A, elevation actuator 130 is a stepper motor mounted to carriage 102 that drives a pinion 132, which meshes with and drives a spur gear 134 formed about gamma ray source 110.

Downhole tool 100 may also include a gamma ray detector 140. In one or more embodiments, gamma ray detector 140 is disposed within housing 106. In one or more embodiments, gamma ray detector 140 may be a photo-multiplied scintillation detector, such as that described in greater detail hereinafter with respect to FIG. 5. However, any other type of suitable gamma ray detector 140 may be used, and the disclosure is not limited to a particular gamma ray detector 140. In one or more embodiments, a detector collimator 150 may be included as part of gamma ray detector 140 and the pair oriented so that gamma ray detector 140 substantially receives only gamma rays incident at a detection elevation angle β with respect to housing 106. Gamma ray detector 140 may be rigidly mounted on carriage 102 at a longitudinal distance d from gamma ray source 110.

In one or more embodiments, gamma ray detector 140 may be rotatively mounted in order to selectively adjust detection elevation angle β. Adjustment may be useful for tool calibration purposes, for example.

Figure 3B:
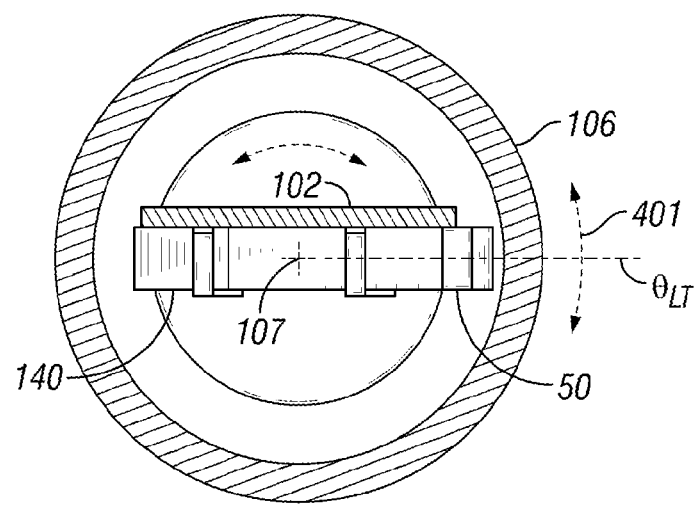
FIG. 3B is a transverse cross section of the downhole logging tool of FIG. 3A taken along line 3B-3B of FIG. 3A.

Referring to FIGS. 3A and 3B, gamma ray source 110 and gamma ray detector 140 may be positioned to emit and detect collimated gamma rays within a common azimuthal plane, which may be, but need not necessarily be, defined in relation to carriage 102. In one embodiment (not specifically illustrated), carriage 102 may be fixed in relation to housing 106 to define a logging tool azimuthal angle $\theta_{LT}$ for emission and detection of gamma rays that is fixed in relation to housing 106.

In another embodiment, carriage 102 may be selectively rotatable about a longitudinal axis 107, so that logging tool azimuthal angle $\theta_{LT}$ may be selectively controlled with respect to housing 106, as illustrated by arrow 401 (FIG. 3B). Carriage 102 may be rotatively mounted by upper and lower bearings 103a, 103b, which may in turn be mounted to the interior of housing 106 by upper and lower bulkhead brackets 105a, 105b. Carriage 102 may be connected by shaft through bearing 103 to an azimuthal actuator 135, which may be used to rotate carriage 102, and concomitantly gamma ray source 110 and detector 140, within housing 106. Azimuthal actuator 135 may include a servo motor, a stepper motor, or other suitable device.

Gamma ray source 110 may require a vacuum source for operation. A vacuum pump 111 may be provided. Vacuum pump may be connected directly to gamma ray source 110 (not illustrated), or it may be mounted to carrier 102 and fluidly connected to gamma ray source 110 via flexible hose 112. Other suitable arrangements may also be provided.

Gamma ray source 110 and/or gamma ray detector 140 may also require a high-voltage power supply. Accordingly, a power supply 114 may be provided. Power supply 114 may be mounted to carrier 102. Power supply 114 may also provide power to elevation and azimuthal actuators 130, 135, vacuum pump 111, and to a controller 116.

Controller 116 may include a processor, memory, input/output circuitry, drivers, and other control circuitry for controlling logging tool 100. Controller 116 may be arranged to enable and disable gamma ray source 110 and detector 140, to receive measurement signals from gamma ray detector 140, to compute count ratios, to control elevation and azimuthal actuators 130, 135, and to communicate with other tools and/or the surface via telemetry. Controller 116 may be mounted to carrier 102.

Figure 4:
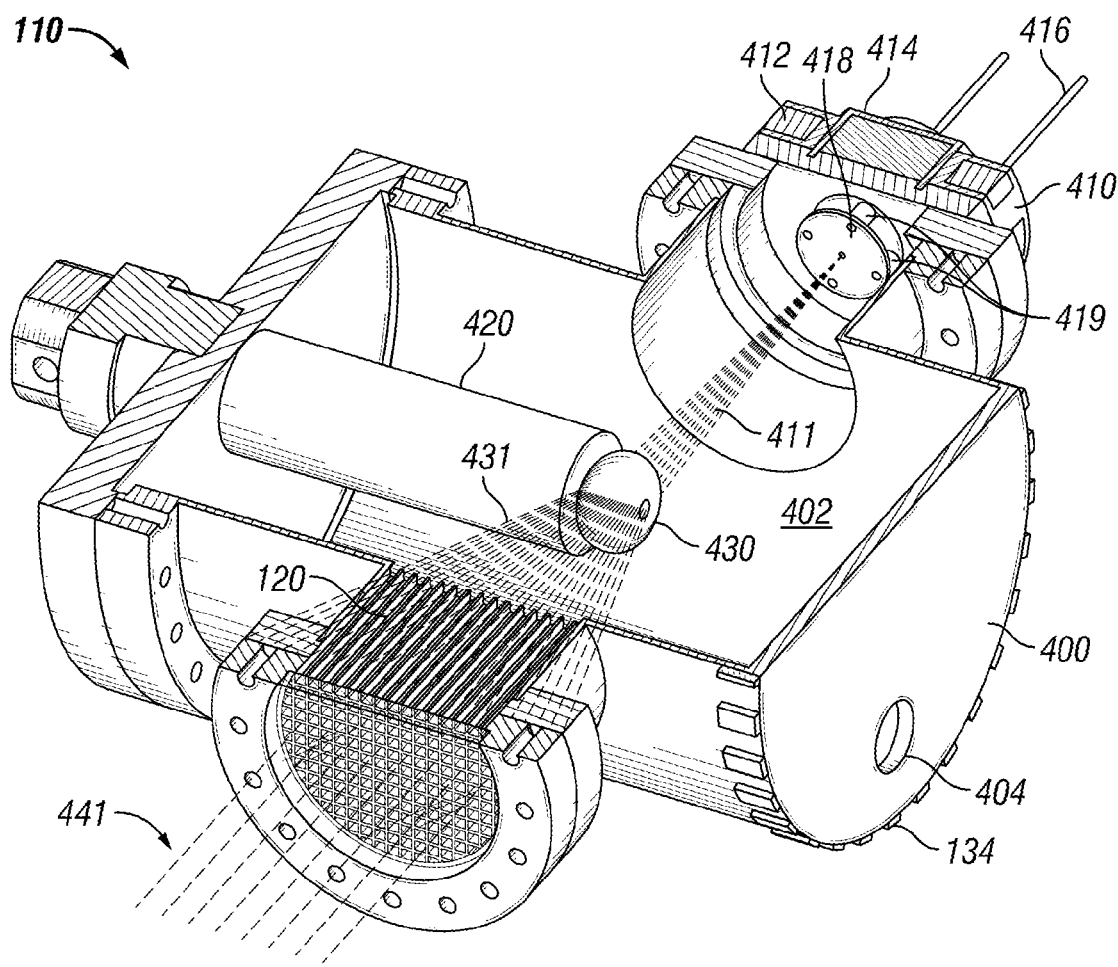
FIG. 4 is a perspective view in cross section of a compact collimated electronic gamma ray source according to an embodiment, which may be used with the downhole logging tool of FIG. 3A.

FIG. 4 is a perspective view in cross section of one embodiment of an electronic gamma ray source 110 for use within logging tool 100 (FIG. 3A). Gamma ray source 110 may include a sealed vessel 400 defining a chamber 402. Vessel 400 may include a port 404 for connection to a vacuum pump 111 (FIG. 3A). Alternatively, a vacuum pump may be directly affixed to vessel 400 (not illustrated).

Gamma ray source 110 may include an ion source 410, an accelerator 420, and a gamma production target 430. Ions 411 produced from ion source 410 may be accelerated through chamber 402 onto production target 430, thereby creating gamma rays 431. Gamma rays 431 may be filtered through source collimator 120 to produce collimated gamma rays 441.

In an embodiment, ion source 410 may be a radio frequency discharge plasma ion source, which may include a magnet array 412 that at least partially surrounds a quartz plasma chamber 414, a radio frequency antenna 416, and an extraction electrode 418. Plasma clamber 414 may be filled with deuterium gas. Radio frequency antenna 416 may be coupled to plasma chamber 414 so that application of a radio frequency on antenna 416 field produces a $D^+$ plasma ion gas within plasma chamber 414. Magnet array 412 may provide for better plasma confinement. Magnet array 412 may be circular and may include a number of neodymium-iron-boron magnets. Other magnet types and arrangements may also be used as appropriate. Extraction electrode 418 may be insulated from plasma chamber 414 by ceramic standoffs 419. An extraction voltage may be applied to extraction electrode 418 to extract $D^+$ ions from plasma chamber 414 into chamber 402.

In an embodiment, accelerator 420 may be a pyroelectric crystal accelerator including a $LiTaO_3$ or like crystal housed in a polythermide tube. A fluid path (not illustrated) may be provided within the polythermide tube for heating and cooling purposes. Accelerator 420 may be mounted within chamber 420 by a first end, which may be grounded to vessel 400. A second end may carry gamma production target 430, which may include $^9Be$ material. A high voltage may be applied to gamma production target 430 by the pyroelectric crystal when the crystal is heated, thereby creating a strong electric field within chamber 402 for accelerating ions 411 onto gamma production target 430.

In an embodiment, source collimator 120 may be provided and positioned within the beam of produced gamma rays 431 emitted by gamma ray target 430. Source collimator 120 may be a sheet of lead, or other material opaque to the incoming gamma rays 431, with many tiny parallel elongate holes formed therethrough, thereby producing the collimated gamma rays 441. Meshes, screens, honeycomb, or other structures may also be suitable for source collimator 120.

As described herein, electronic gamma ray source 110 may be capable of producing gamma rays with energies ranging from approximately 400 keV to 3 MeV, depending on the particular arrangement and voltages used. However, other gamma rays sources 110 may be used, including a radionuclide source housed within a shielded enclosure having a window that may be selectively opened (not illustrated).

Figure 5:
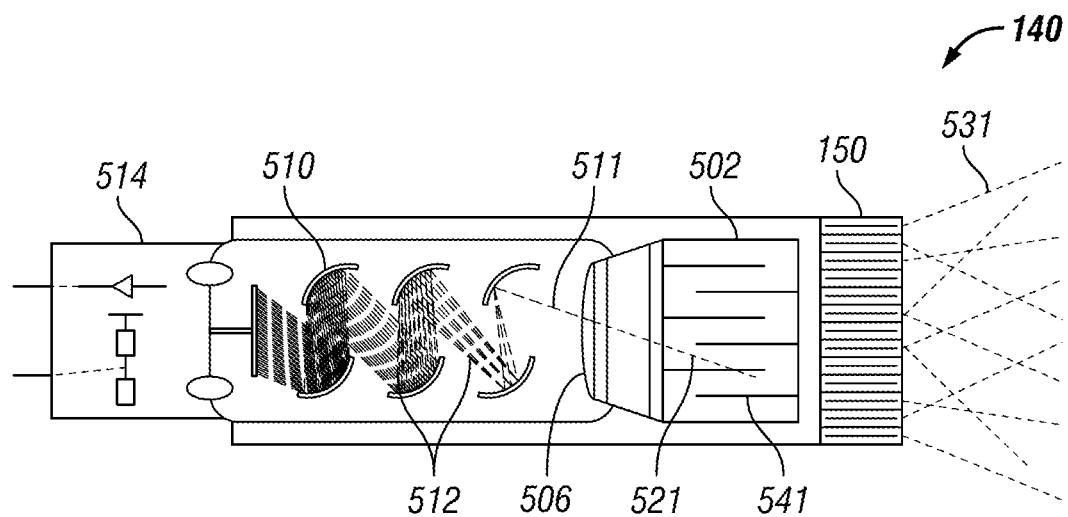
FIG. 5 is a functional block diagram of a photo-multiplied gamma ray detector according to an embodiment, which may be used with the downhole logging tool of FIG. 3A.

FIG. 5 is a functional block diagram of gamma ray detector 140 according to an embodiment for use within logging tool 100 (FIG. 3A). Gamma ray detector 140 may include a detector collimator 150, which may be a sheet of lead, or other material opaque to the incoming gamma rays 531, with many tiny parallel elongate holes formed therethrough, thereby minimizing the detection sensitivity of gamma ray detector 140 to gamma rays incident from other than a desired direction. Meshes, screens, honeycomb, or other structures may also be suitable for detector collimator 150.

Gamma detector 140 may include a scintillator 502, a photocathode 506, and a photomultiplier 510. Scintillator 502 may be coupled between detector collimator 150 and photocathode 506 and operable to receive incident gamma rays 541 and in response emit luminous photons 521. Photocathode 506 may be operable to receive luminous photons 521 and in response emit photoelectrons 511. Photomultiplier 510 may be coupled to photocathode 506 and operable to receive photoelectrons 511 and in response emit multiple secondary photoelectrons 512. The output of photomultiplier 510 may be connected to counting and amplification circuitry 514. However, although a photo-multiplied scintillation detector is disclosed herein, any suitable type of gamma ray detector 140 may be used as appropriate.

Figure 6:
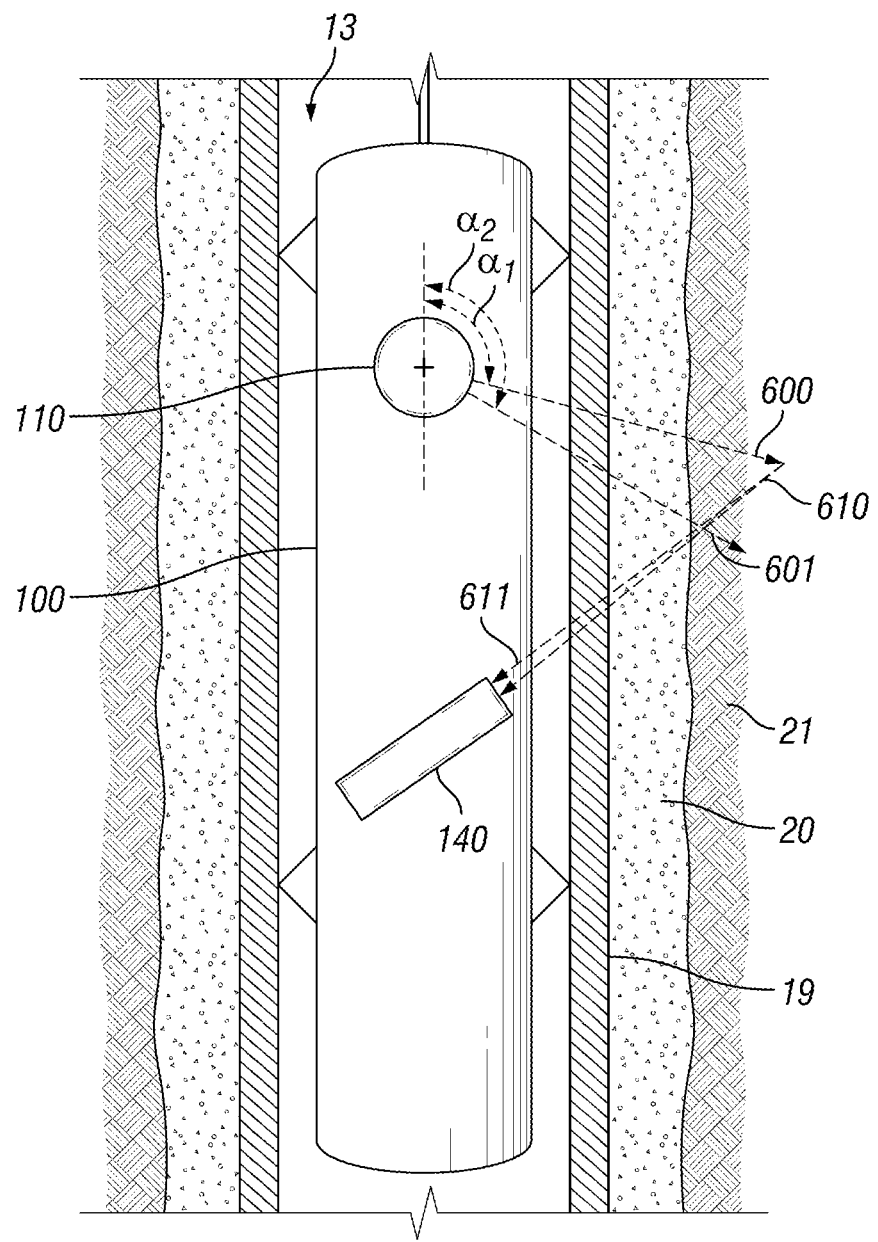
FIGS. 6 and 7 are functional block diagrams of the downhole logging tool of FIG. 3A shown within a cased and cemented wellbore, which may be used for carrying out the method of FIG. 8.
Figure 7:
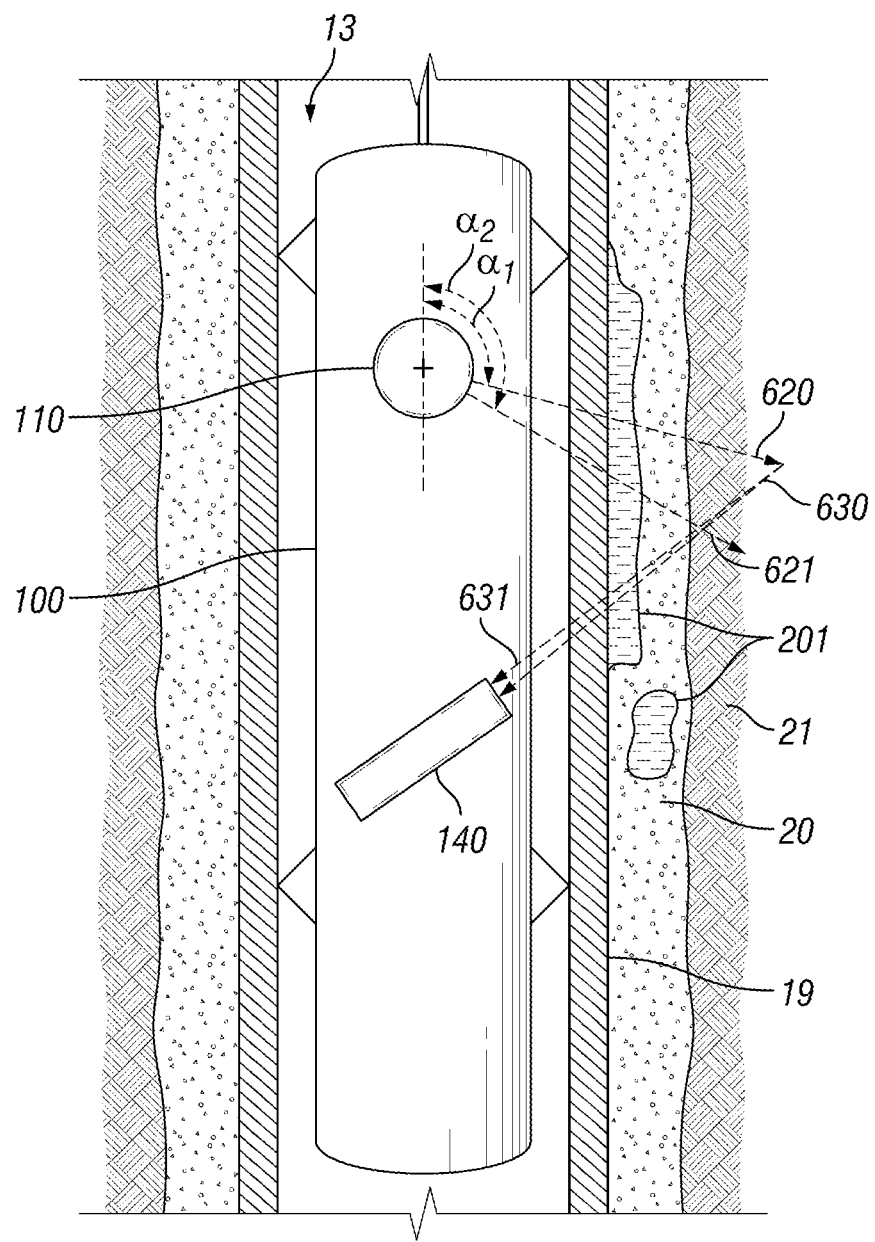
Figure 8:
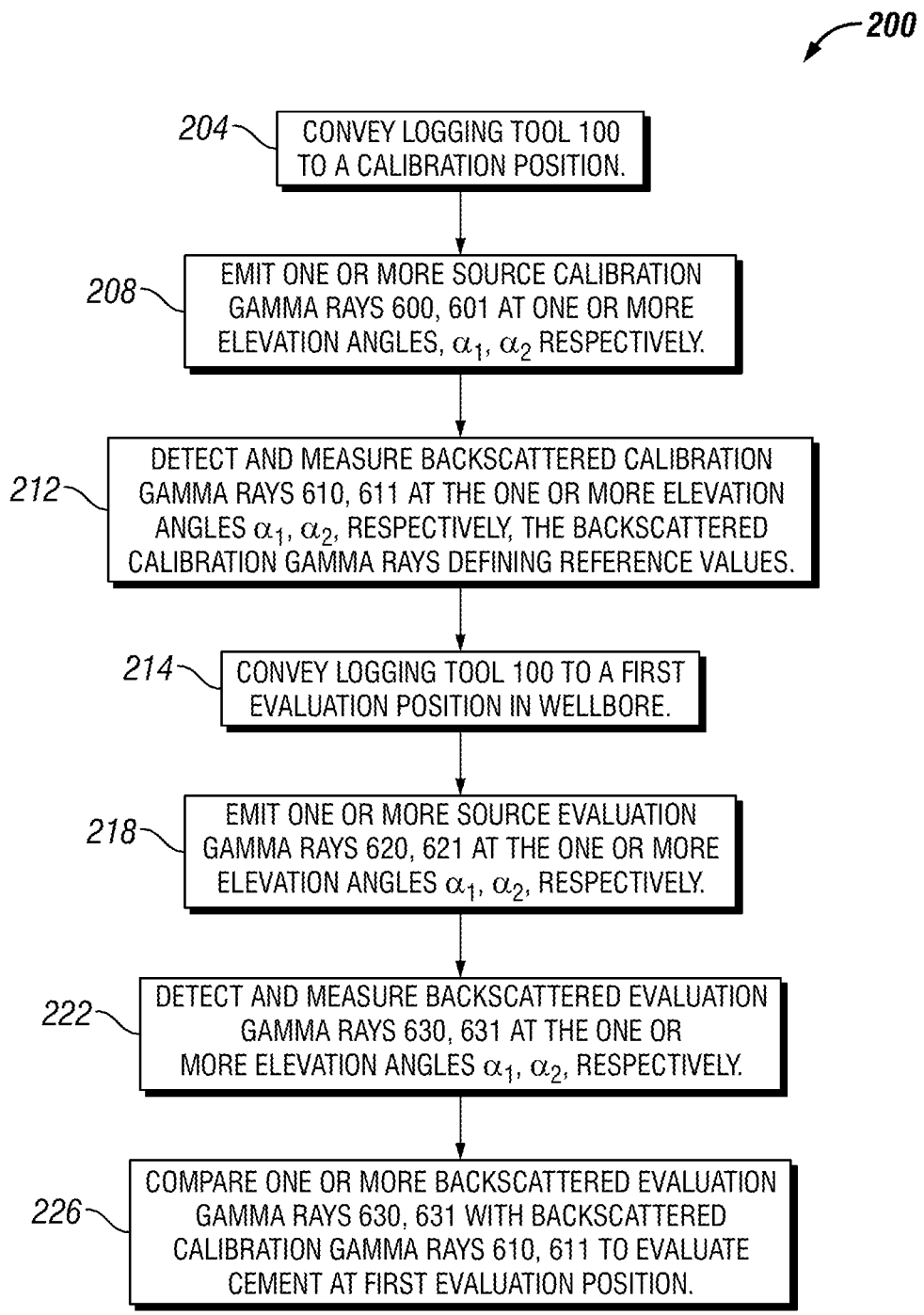
FIG. 8 is a flowchart of a method for evaluating characteristics of cement within a wellbore according to an embodiment.

FIGS. 6 and 7 are simplified elevation views of logging tool 100 disposed within differing sections of wellbore 13. In FIG. 6, logging tool 100 is located within a calibration region of wellbore 13 that is known to have an acceptable cement layer 20 between casing 19 and formation 21, that is, bonded to both the casing and the formation, and homogeneous throughout. In FIG. 7, logging tool 100 is located within a first evaluation region of wellbore 13. In this particular exemplary figure, cement layer 20 includes discontinuities or voids 201, which may be filled with a fluid and which illustrate both the conditions of insufficient bonding and inhomogeneity in the cement layer. FIG. 8 is a flowchart of a method 200 for evaluating cement 20 in wellbore 13 between casing 19 and formation 21 according to an embodiment.

Referring now to FIGS. 6 and 8, in operation, in one or more embodiments, at step 204, logging tool 100 is lowered to a calibration depth, by wireline string, or other conveyance into casing 19 where there is known to be a satisfactory cement 20 layer between casing 19 and formation 21. FIG. 6 illustrates logging tool 100 in the calibration position.

At step 208, a first source calibration gamma ray 600 is emitted by gamma ray source 110 at a first elevation angle $\alpha_1$. In one or more embodiments, angle $\alpha_1$ may range from 75 degrees to 225 degrees from centerline 107. First source gamma calibration ray 600 may pass through whatever fluid may be located within wellbore 13, through casing 19, cement 20, and into formation 21. At step 212, a portion 610 of first source calibration gamma ray 600 may be backscattered and received by gamma ray detector 140. In one or more embodiments, this first backscattered calibration gamma ray 610 may be measured and correlated with elevation angle $\alpha_1$ for later use as a reference value.

In one or more embodiments, gamma ray source 110 is rotated to a second position, and repeating step 208, a second source calibration gamma ray 601 is emitted by gamma ray source 110 at a second elevation angle $\alpha_2$. As before, at step 212, a second backscattered gamma calibration ray 611 may be received by gamma ray detector 140. Second backscattered calibration gamma ray 611 may be measured and correlated with elevation angle $\alpha_2$ for later use as a reference value.

In one or more embodiments, at step 208, source calibration gamma rays may be continuously emitted as gamma ray source 110 is moved through a range of elevation angles $\alpha$. Likewise, at step 212, backscattered gamma calibration rays may continuously detected, measured, and recorded as reference values.

In one or more embodiments, downhole logging tool 100 is then rotated within wellbore 13, or gamma ray source 110 and gamma ray detector 140 may be rotated within logging tool 100 to one or more azimuthal angles. At each new azimuth, the elevation scan may be repeated until full 360 degree coverage is obtained at the calibration position.

Although calibration of downhole logging tool 100 is described as occurring within a calibration section of wellbore 13, calibration may occur in a lab setting, test bed, or other wellbore. Moreover, calibration steps 204, 208, and 212 are shown as beginning steps of evaluation method 200. However, steps 204, 208, and 212 may occur after other wellbore evaluation steps have been fully or partially performed. Alternatively, one or more steps in the calibration process may be eliminated and a standard set of calibration data may be used.

Referring now to FIGS. 7 and 8, in operation, at step 214, logging tool 100 is lowered to a first depth in wellbore 13 in which the cement 20 layer between casing 19 and formation 21 is to be evaluated. FIG. 7 illustrates logging tool 100 in this first evaluation position.

At step 218, a first source evaluation gamma ray 620 may be emitted by gamma ray source 110 at the first elevation angle $\alpha_1$. First source gamma evaluation ray 620 may pass through fluid located within wellbore 13, through casing 19, cement 20, and into formation 21. At step 222, a portion 630 of first source evaluation gamma ray 620 may be backscattered and received by gamma ray detector 140. This first backscattered evaluation gamma ray 630 may be measured and in step 226 may be compared in real time or during subsequent processing with the $\alpha_1$ reference value—that is, with the first backscattered calibration gamma ray 610—to identify discontinuity 201 in cement 20.

In one or more embodiments, gamma ray source 110 may be rotated to the second position, and repeating step 218, a second source evaluation gamma ray 621 is emitted by gamma ray source 110 at the second elevation angle $\alpha_2$. As before, at step 222, a second backscattered gamma evaluation ray 631 may be received by gamma ray detector 140. Second backscattered evaluation gamma ray 631 may be measured and in step 226 may be compared in real time or during subsequent processing with the $\alpha_2$ reference value— that is, the second backscattered calibration gamma ray 611—to identify discontinuities in cement 20.

In one or more embodiments illustrated at step 218, source evaluation gamma rays may be continuously emitted as gamma ray source 110 is moved through a range of elevation angles $\alpha$. Likewise, at step 222, backscattered gamma evaluation rays may be continuously detected, and measured. In step 226, backscattered gamma evaluation rays may be compared, either in real time or during subsequent processing, with the backscattered calibration gamma rays measured at corresponding elevation angles $\alpha$ to identify discontinuities in cement 20.

In an embodiment, logging tool 100 may then be rotated within wellbore 13, or gamma ray source 110 and gamma ray detector 140 may be rotated within logging tool 100. At each new azimuth, the elevation scan may be repeated until full 360 degree coverage is obtained at the first evaluation position in wellbore 13. Logging tool 100 may then be conveyed to a second depth in wellbore 13 in which the cement 20 layer between casing 19 and formation 21 is to be evaluated, and the above-described process repeated until desired sections of cement 20 have been evaluated.

Figure 9:
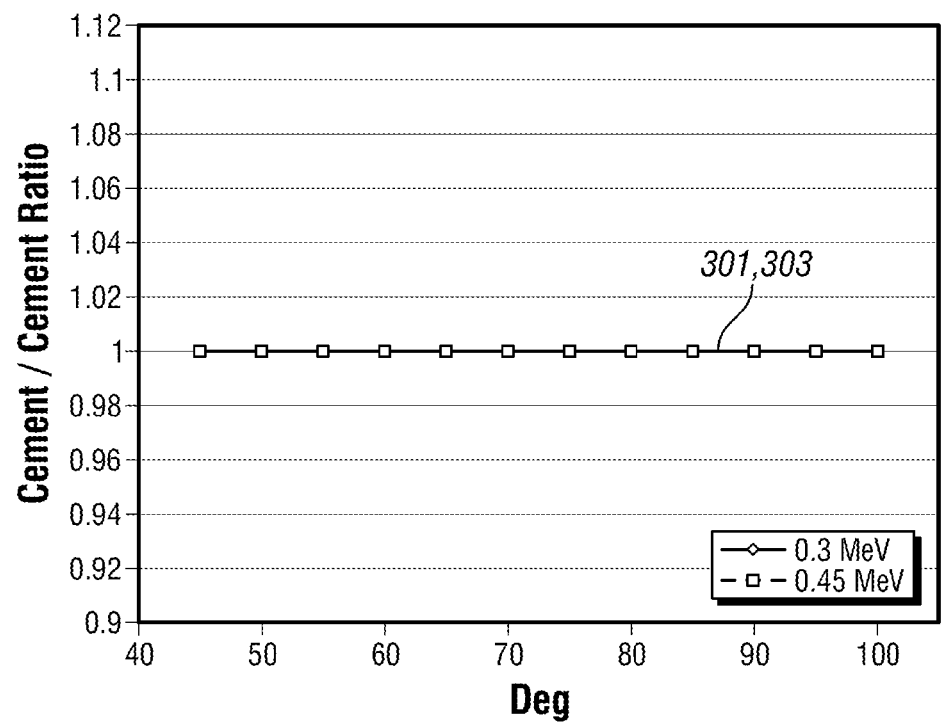
FIGS. 9 and 10 are plots of measured gamma rays according to the method of FIG. 8.
Figure 10:
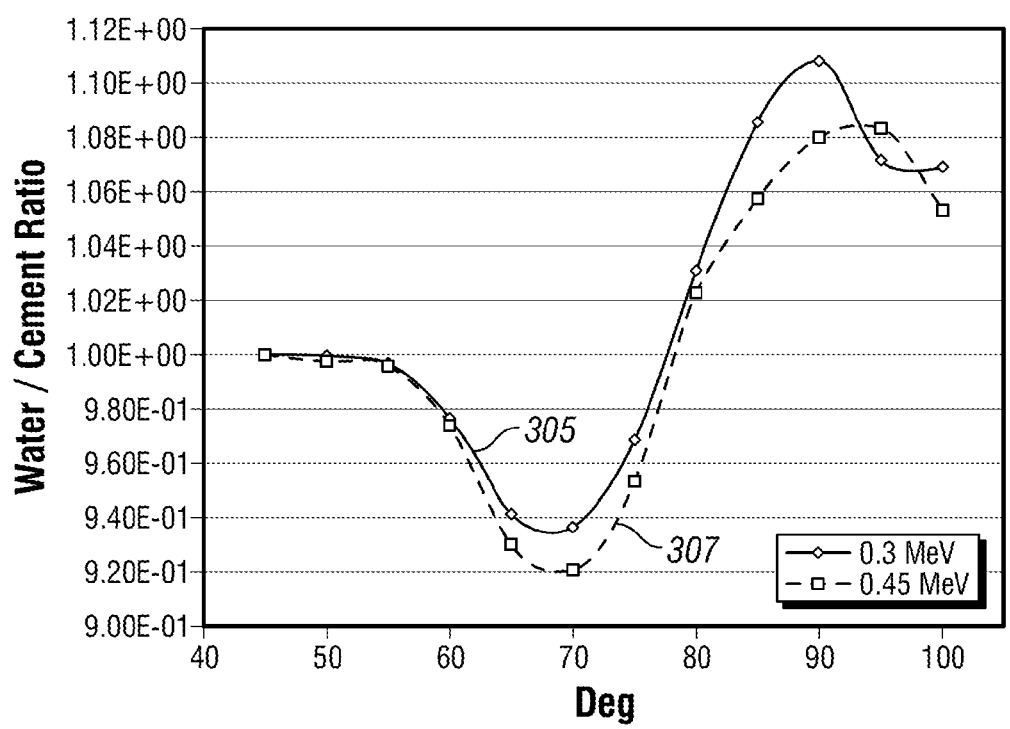

FIGS. 9 and 10 are plots of measured gamma rays according to the method of FIG. 8. Referring to FIGS. 8 and 9, at step 226, backscattered evaluation gamma rays may be compared with backscattered calibration gamma rays measured at corresponding elevation angles $\alpha$. In an embodiment, for each elevation angle $\alpha$, a ratio of the measured backscattered evaluation gamma ray to the measured backscattered calibration gamma ray may be computed. The computed ratios may be plotted as a function of the elevation angle $\alpha$, as shown in FIG. 9.

The ratios plotted in FIG. 9 each have a value of approximately unity. Provided that the calibration data was measured in a region with known good cement, such a result as that of FIG. 9 may be indicative of homogeneous cement 20 with no voids, inclusions or discontinuities. Method 200 may be independent of gamma ray energy levels, as illustrated by substantially overlapping ratio plots 301, 303 corresponding to two different source gamma ray energy levels.

FIG. 10 is a plot of computed backscattered evaluation to backscattered calibration gamma rays corresponding to an evaluation region of the wellbore that has poor cement bonding or a void in the cement layer, such as void 201 in FIG. 7. Referring to FIGS. 7 and 10, as indicated, plotted computed ratios 305, 307 have values less than unity at elevation angles $\alpha$ between approximately 55 and 78 degrees and values greater than unity above 78 degrees. Again, the trend may be relatively independent of source gamma ray energy levels. Non-unity backscattered evaluation to backscattered calibration gamma ray ratios may indicate discontinuities in cement 20.

Although backscattered evaluation to backscattered calibration gamma ray ratios may be computed and plotted, other ways of displaying and interpreting this data may also be used. For instance, backscattered evaluation and/or calibration gamma rays may be plotted as a function of color or gray scale to represent the density distributions in the annulus between casing 19 and formation 21.

In summary, methods and a logging tool for evaluating cement in a wellbore behind a casing have been described. Embodiments of a method may generally include: Conveying a logging tool to a first position in the wellbore; emitting from the first position a first source evaluation gamma ray at a first elevation angle with respect to the logging tool; detecting a first backscattered evaluation gamma ray from the first source evaluation gamma ray; measuring the first backscattered evaluation gamma ray; and comparing the measured first backscattered evaluation gamma ray to a first reference value to evaluate the cement at the first position in the wellbore. Embodiments of a method may also generally include: Conveying a logging tool to a first position in the wellbore; emitting from the first position a first set of collimated source evaluation gamma rays within the wellbore at a plurality of elevation angles with respect to a centerline of the wellbore; at each of the plurality of elevation angles, detecting and measuring a first set of backscattered evaluation gamma rays from the first set of collimated source evaluation gamma rays; and comparing the first set of measured backscattered evaluation rays to a plurality of reference values to evaluate the cement. Embodiments of a logging tool may generally have: A housing; a gamma ray source pivotally disposed within the housing and movable between selectively controlled elevation angles with respect to the housing; a gamma ray detector disposed within the housing; and a controller arranged for measuring an output of the gamma ray detector.

Any of the foregoing embodiments may include any one of the following, alone or in combination with each other: Conveying the logging tool to a calibration position in the wellbore; emitting from the calibration position a first source calibration gamma ray at the first elevation angle; detecting a first backscattered calibration gamma ray from the first calibration source gamma ray; measuring the first backscattered calibration gamma ray to define the first reference value; computing a ratio of the measured first backscattered evaluation gamma ray to the measured first backscattered calibration gamma ray to evaluate the cement; emitting a second source calibration gamma ray within the wellbore at a second elevation angle with respect to the logging tool at the calibration position in the wellbore; detecting a second backscattered calibration gamma ray from the second calibration source gamma ray; measuring the second backscattered calibration gamma ray; emitting from the first position a second source evaluation gamma ray within the wellbore at the second elevation angle; detecting a second backscattered evaluation gamma ray from the second source evaluation gamma ray; measuring the first backscattered evaluation gamma ray; comparing the measured second backscattered evaluation gamma ray to the measured second backscattered calibration gamma ray to evaluate the cement at the first position in the wellbore; orienting a gamma ray source at the first elevation angle to produce the first source evaluation gamma ray and the first source calibration gamma ray; orienting the gamma ray source at the second elevation angle to produce the second source evaluation gamma ray and the second source calibration gamma ray; rotating the gamma ray source from the first elevation angle to the second elevation angle; collimating an output of the gamma ray source; detecting the first and second backscattered evaluation gamma rays and the first and second backscattered calibration gamma rays by a gamma ray detector oriented at a fixed detection elevation angle with respect to the logging tool; collimating an input of the gamma ray detector; orienting a fixed logging tool azimuthal angle with a first wellbore azimuth; emitting the first and second source evaluation gamma rays at the fixed logging tool azimuthal angle and the first wellbore azimuth; detecting the first and second backscattered evaluation gamma rays at the fixed logging tool azimuthal angle and the first wellbore azimuth; rotating the logging tool within the wellbore to orient the fixed logging tool azimuthal angle with a second wellbore azimuth; emitting a third source evaluation gamma ray at the fixed logging tool azimuthal angle and the second wellbore azimuth; detecting a third backscattered evaluation gamma ray from the third source evaluation gamma ray at the fixed logging tool azimuthal angle and the second wellbore azimuth; while maintaining the logging tool stationary within the wellbore, emitting the first and second source evaluation gamma rays at a first logging tool azimuthal angle with respect to the logging tool, detecting the first and second backscattered evaluation gamma rays at the first logging tool azimuthal angle, emitting a third source evaluation gamma ray at a second logging tool azimuthal angle, and detecting a third backscattered evaluation gamma ray from the third source evaluation gamma ray at the second logging tool azimuthal angle; emitting the first source evaluation gamma ray by a gamma ray source; detecting the first backscattered evaluation gamma ray by a gamma ray detector; carrying the a gamma ray source and the gamma ray detector on a carriage within the logging tool; selectively rotating the carriage about a longitudinal axis; producing an ion beam; accelerating the ion beam; striking a target with the accelerated ion beam to emit the first source evaluation gamma ray; receiving the first backscattered evaluation gamma ray by a scintillator; amplifying an output of the scintillator by a photomultiplier; conveying the logging tool to a calibration position in the wellbore; emitting from the calibration position a set collimated source calibration gamma rays within the wellbore at the plurality of elevation angles with respect to a centerline of the wellbore; at each of the plurality of elevation angles, detecting and measuring backscattered calibration gamma rays from the source calibration gamma rays to define the plurality of reference values; emitting the first set of collimated source evaluation gamma rays at a first azimuth of the wellbore; detecting and measuring the first set of backscattered evaluation gamma rays at the first azimuth of the wellbore; emitting a second set of collimated source evaluation gamma rays within the wellbore at the plurality of elevation angles and at a second azimuth of the wellbore; at each of the plurality of elevation angles, detecting and measuring a second set of backscattered evaluation gamma rays from the second set of source evaluation gamma rays at the second azimuth of the wellbore; comparing the second set of measured backscattered evaluation rays to the plurality of reference values to evaluate the cement at the second azimuth of the wellbore; plotting a mathematical function of the first set of measured backscattered evaluation rays; the gamma ray source includes a source collimator; the gamma ray detector includes a detector collimator; an elevation actuator coupled to the gamma ray source to position the gamma ray source at the selectively controlled elevation angles; a carriage disposed within the housing and carrying the gamma ray source and the gamma ray detector; an azimuthal actuator coupled to the carriage to position the gamma ray source and the gamma ray detector at selectively controlled azimuthal angles with respect to the housing; the gamma ray source includes a radio frequency discharge plasma ion source, a pyroelectric crystal accelerator, and a gamma production target, the ion source capable of producing an ion beam, the ion beam accelerative by the accelerator to strike the gamma production target and thereby produce a gamma ray; the gamma ray source further includes a vessel that defines a vacuum chamber; the ion source includes a magnet array that at least partially surrounds a plasma chamber, a radio frequency antenna, and an extraction electrode; the gamma ray detector includes a scintillator, a photocathode, and a photomultiplier; the scintillator is operable to receive a gamma particle and produce a luminous photon; the photocathode is optically coupled to the scintillator and operable to receive the luminous photon and produce a photoelectron; and the photomultiplier is coupled to the photo cathode and operable to receive the photoelectron and produce multiple secondary photoelectrons.

While various embodiments have been illustrated in detail, the disclosure is not limited to the embodiments shown. Modifications and adaptations of the above embodiments may occur to those skilled in the art. Such modifications and adaptations are in the spirit and scope of the disclosure.

What is claimed:

1. A method for evaluating cement in a wellbore behind casing, comprising:
   conveying a logging tool to a first position in the wellbore, the logging tool being operable to emit source evaluation gamma rays at a plurality of elevation angles while in the first position;
   emitting from the first position a first source evaluation gamma ray at a first elevation angle with respect to said logging tool;
   detecting a first backscattered evaluation gamma ray from said first source evaluation gamma ray;
   measuring said first backscattered evaluation gamma ray; and
   comparing said measured first backscattered evaluation gamma ray to a first reference value to evaluate said cement at said first position in the wellbore.
2. The method of claim 1 further comprising:
   conveying said logging tool to a calibration position in the wellbore;
   emitting from the calibration position a first source calibration gamma ray at said first elevation angle;
   detecting a first backscattered calibration gamma ray from said first calibration source gamma ray; and
   measuring said first backscattered calibration gamma ray to define said first reference value.
3. The method of claim 2 further comprising:
   computing a ratio of said measured first backscattered evaluation gamma ray to said measured first backscattered calibration gamma ray to evaluate said cement.
4. The method of claim 1 further comprising:
   emitting a second source calibration gamma ray within said wellbore at a second elevation angle with respect to said logging tool at said calibration position in the wellbore;
   detecting a second backscattered calibration gamma ray from said second calibration source gamma ray;
   measuring said second backscattered calibration gamma ray;
   emitting from said first position a second source evaluation gamma ray within said wellbore at said second elevation angle;
   detecting a second backscattered evaluation gamma ray from said second source evaluation gamma ray;
   measuring said first backscattered evaluation gamma ray; and
   comparing said measured second backscattered evaluation gamma ray to said measured second backscattered calibration gamma ray to evaluate said cement at said first position in the wellbore.
5. The method of claim 4 further comprising:
   orienting a gamma ray source at said first elevation angle to produce said first source evaluation gamma ray and said first source calibration gamma ray; and
   orienting said gamma ray source at said second elevation angle to produce said second source evaluation gamma ray and said second source calibration gamma ray.
6. The method of claim 5 further comprising:
   rotating said gamma ray source from said first elevation angle to said second elevation angle.
7. The method of claim 5 further comprising:
   collimating an output of said gamma ray source.
8. The method of claim 5 further comprising:
   detecting said first and second backscattered evaluation gamma rays and said first and second backscattered calibration gamma rays by a gamma ray detector oriented at a fixed detection elevation angle with respect to said logging tool.
9. The method of claim 8 further comprising:
   collimating an input of said gamma ray detector.
10. The method of claim 4 further comprising:
    orienting a fixed logging tool azimuthal angle with a first wellbore azimuth;
    emitting said first and second source evaluation gamma rays at said fixed logging tool azimuthal angle and said first wellbore azimuth;
    detecting said first and second backscattered evaluation gamma rays at said fixed logging tool azimuthal angle and said first wellbore azimuth; then
    rotating said logging tool within said wellbore to orient said fixed logging tool azimuthal angle with a second wellbore azimuth;
    emitting a third source evaluation gamma ray at said fixed logging tool azimuthal angle and said second wellbore azimuth; and
    detecting a third backscattered evaluation gamma ray from said third source evaluation gamma ray at said fixed logging tool azimuthal angle and said second wellbore azimuth.
11. The method of claim 4 further comprising:
    while maintaining said logging tool stationary within said wellbore,
    emitting said first and second source evaluation gamma rays at a first logging tool azimuthal angle with respect to said logging tool,
    detecting said first and second backscattered evaluation gamma rays at said first logging tool azimuthal angle,
    emitting a third source evaluation gamma ray at a second logging tool azimuthal angle, and
    detecting a third backscattered evaluation gamma ray from said third source evaluation gamma ray at said second logging tool azimuthal angle.
12. The method of claim 1 further comprising:
    emitting said first source evaluation gamma ray by a gamma ray source;
    detecting said first backscattered evaluation gamma ray by a gamma ray detector;
    carrying said a gamma ray source and said gamma ray detector on a carriage within said logging tool; and
    selectively rotating said carriage about a longitudinal axis.
13. The method of claim 1 further comprising:
    producing an ion beam;
    accelerating said ion beam; and striking a target with said accelerated ion beam to emit said first source evaluation gamma ray.

14. The method of claim 1 further comprising:
receiving said first backscattered evaluation gamma ray by a scintillator; and
amplifying an output of said scintillator by a photomultiplier.

15. A method for evaluating cement in a wellbore behind casing, comprising:
conveying a logging tool to a first position in the wellbore;
emitting from the first position a first set of collimated source evaluation gamma rays within said wellbore at a plurality of elevation angles with respect to a centerline of said wellbore;
at each of said plurality of elevation angles, detecting and measuring a first set of backscattered evaluation gamma rays from said first set of collimated source evaluation gamma rays; and
comparing said first set of measured backscattered evaluation rays to a plurality of reference values to evaluate said cement.

16. The method of claim 15 further comprising:
conveying said logging tool to a calibration position in the wellbore;
emitting from the calibration position a set collimated source calibration gamma rays within said wellbore at said plurality of elevation angles with respect to a centerline of said wellbore; and
at each of said plurality of elevation angles, detecting and measuring backscattered calibration gamma rays from said source calibration gamma rays to define said plurality of reference values.

17. The method of claim 15 further comprising:
emitting said first set of collimated source evaluation gamma rays at a first azimuth of said wellbore;
detecting and measuring said first set of backscattered evaluation gamma rays at said first azimuth of said wellbore;
emitting a second set of collimated source evaluation gamma rays within said wellbore at said plurality of elevation angles and at a second azimuth of said wellbore;
at each of said plurality of elevation angles, detecting and measuring a second set of backscattered evaluation gamma rays from said second set of source evaluation gamma rays at said second azimuth of said wellbore; and
comparing said second set of measured backscattered evaluation rays to said plurality of reference values to evaluate said cement at said second azimuth of said wellbore.

18. The method of claim 15 further comprising:
plotting a mathematical function of said first set of measured backscattered evaluation rays.

19. A logging tool for evaluating cement in a wellbore behind casing, comprising:
a housing;
a gamma ray source pivotally disposed within said housing and movable between selectively controlled elevation angles with respect to said housing;
a gamma ray detector disposed within said housing; and
a controller arranged for measuring an output of said gamma ray detector.

20. The logging tool of claim 19 wherein:
said gamma ray source includes a source collimator; and
said gamma ray detector includes a detector collimator.

21. The logging tool of claim 19 further comprising:
an elevation actuator coupled to said gamma ray source to position said gamma ray source at said selectively controlled elevation angles.

22. The logging tool of claim 19 further comprising:
a carriage disposed within said housing and carrying said gamma ray source and said gamma ray detector; and
an azimuthal actuator coupled to said carriage to position said gamma ray source and said gamma ray detector at selectively controlled azimuthal angles with respect to said housing.

23. The logging tool of claim 19 wherein:
said gamma ray source includes a radio frequency discharge plasma ion source, a pyroelectric crystal accelerator, and a gamma production target, said ion source capable of producing an ion beam, said ion beam accelerative by said accelerator to strike said gamma production target and thereby produce a gamma ray.

24. The logging tool of claim 23 wherein:
said gamma ray source further includes a vessel that defines a vacuum chamber; and
said ion source includes a magnet array that at least partially surrounds a plasma chamber, a radio frequency antenna, and an extraction electrode.

25. The logging tool of claim 19 wherein:
said gamma ray detector includes a scintillator, a photocathode, and a photomultiplier;
said scintillator is operable to receive a gamma particle and produce a luminous photon;
said photocathode is optically coupled to said scintillator and operable to receive said luminous photon and produce a photoelectron; and
said photomultiplier is coupled to said photo cathode and operable to receive said photoelectron and produce multiple secondary photoelectrons.

* * * * *